(12) United States Patent
Divo et al.

(10) Patent No.: US 6,610,899 B1
(45) Date of Patent: Aug. 26, 2003

(54) ABSORBENT MEMBER AND A METHOD FOR FORMING THE SAME

(75) Inventors: Michael Divo, Friedrichsdorf (DE); Torsten Lindner, Kronberg (DE); Italo Corzani, Chieti (IT)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/674,694

(22) PCT Filed: May 7, 1999

(86) PCT No.: PCT/US99/10006

§ 371 (c)(1),
(2), (4) Date: Nov. 3, 2000

(87) PCT Pub. No.: WO99/56686

PCT Pub. Date: Nov. 11, 1999

(30) Foreign Application Priority Data

May 7, 1998 (EP) .............................................. 98108291

(51) Int. Cl.[7] .............................................. A61F 13/15
(52) U.S. Cl. ................................... 604/367; 604/385.01
(58) Field of Search ................................. 604/367–368, 604/385.01–385.05; 156/205; 428/78, 230

(56) References Cited

U.S. PATENT DOCUMENTS 4,790,838 A * 12/1988 Pigneul et al. .............. 604/366
5,034,007 A * 7/1991 Igaue et al. .................. 156/160
6,007,528 A * 12/1999 Osborn, III .................. 604/368

FOREIGN PATENT DOCUMENTS

| EP | 0 463 716 A2 | 1/1992 | ............ A61F/13/15 |
| EP | 0 700 673 A | 3/1996 | ............ A61F/13/15 |
| GB | 2 004 201 A | 3/1979 | ............ A61F/13/18 |
| WO | WO 96/17574 | 6/1996 | ............ A61F/13/15 |

OTHER PUBLICATIONS

International Search Report dated Mar. 9, 1999 for PCT/US99/10006.

* cited by examiner

Primary Examiner—Weilun Lo
Assistant Examiner—C. Lynne Anderson
(74) Attorney, Agent, or Firm—Mike S. Kolodesh; Jay A. Krebs; Ken K. Patel

(57) ABSTRACT

An absorbent member and a method for forming the absorbent member. A web comprising a fibrous material and superabsorbent material is fed to an applicator. The web has a first side edge and a second side edge. A superabsorbent material movement obstruction agent is applied to the web from the applicator in discrete, spaced apart, continuous zones. The web is then cut through said superabsorbent material movement obstruction agent zones into individual absorbent members having a pair of opposing cut ends.

11 Claims, 3 Drawing Sheets

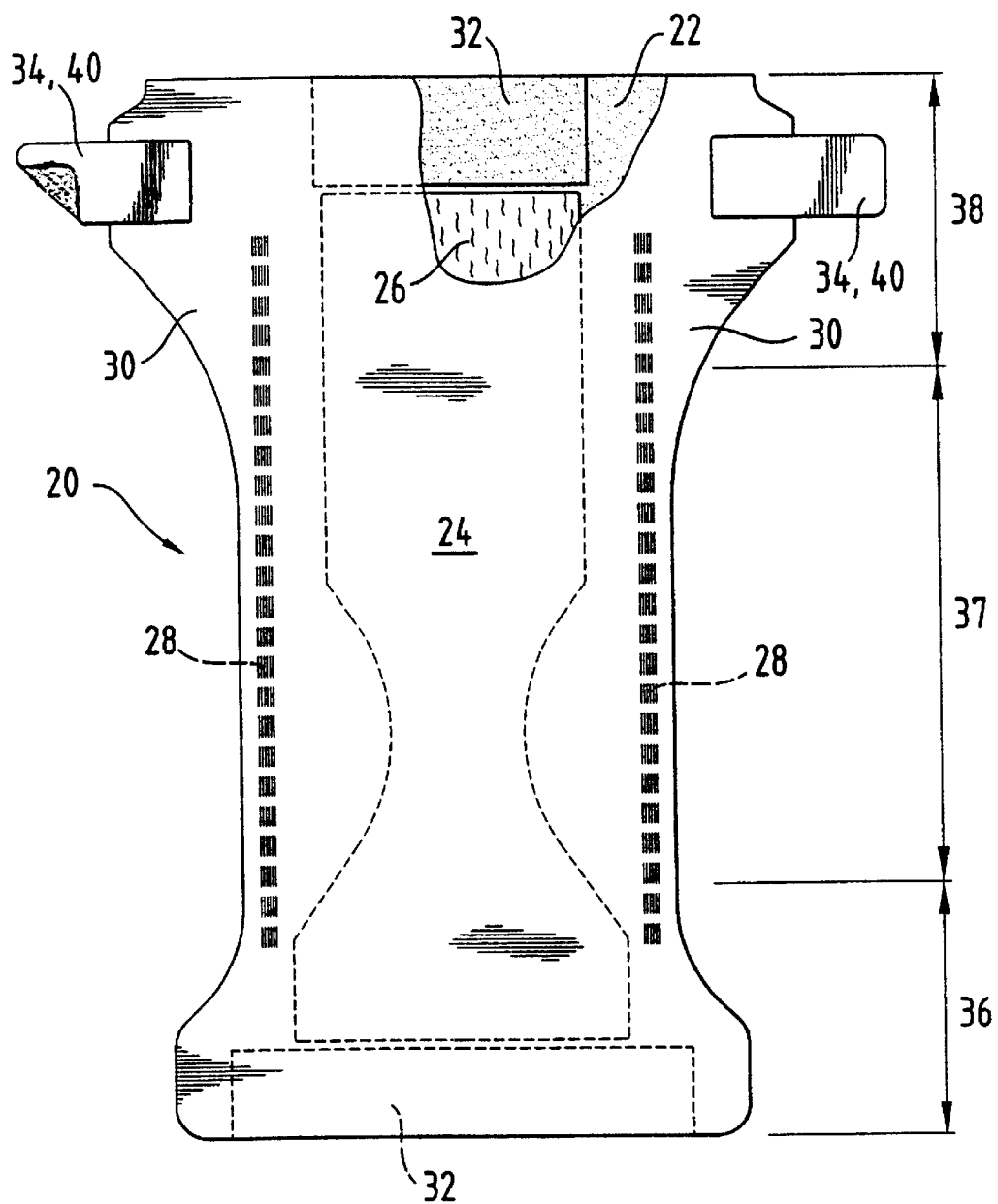

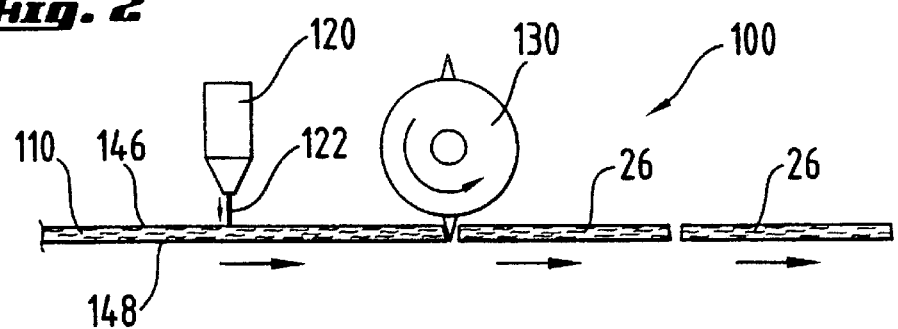
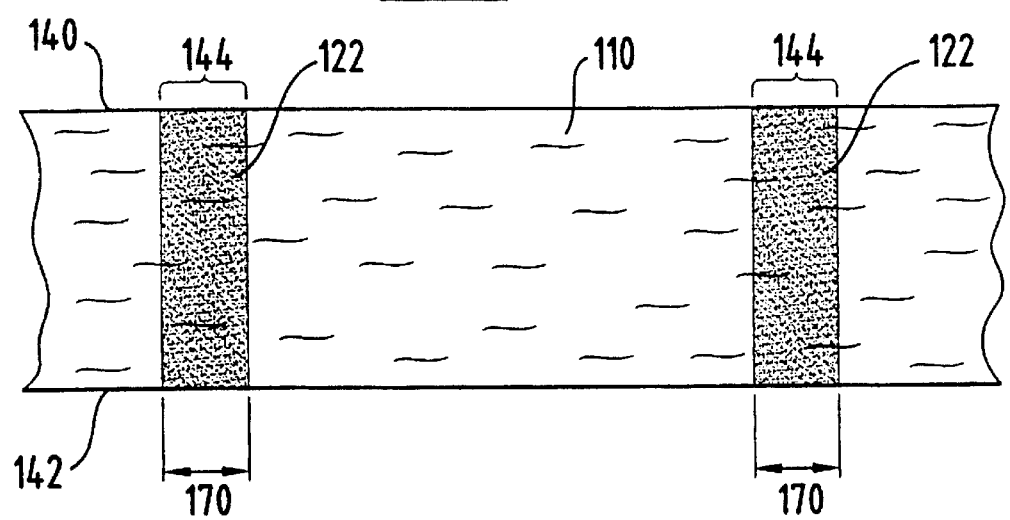
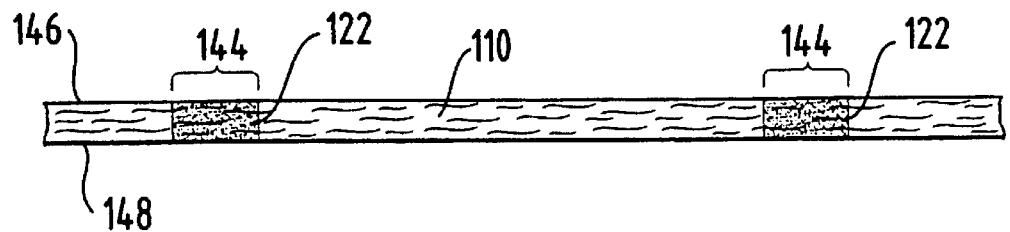

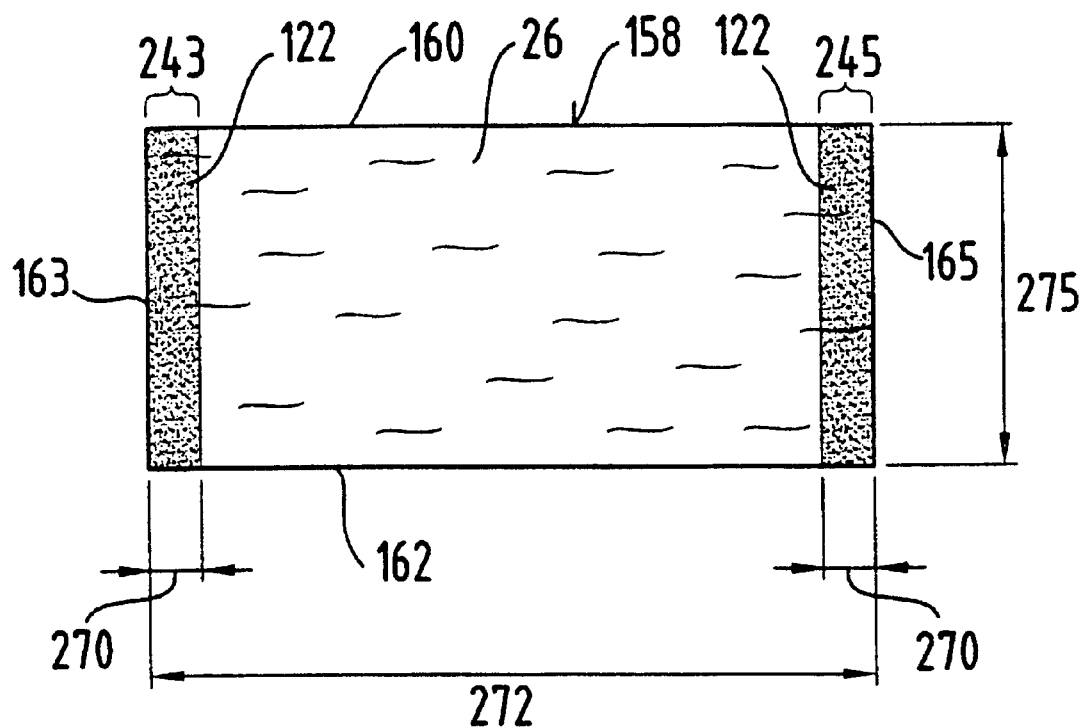
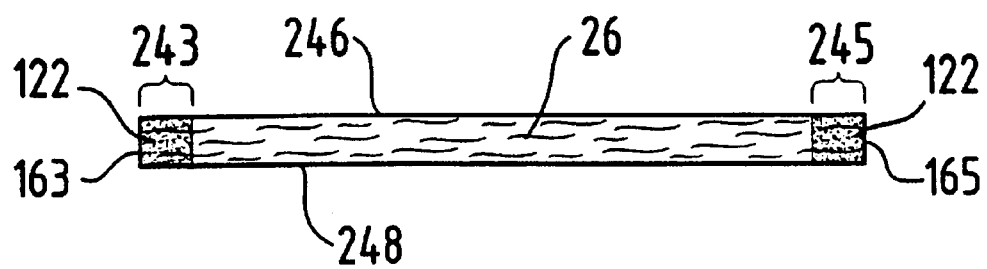

ABSORBENT MEMBER AND A METHOD FOR FORMING THE SAME

FIELD OF THE INVENTION

This invention relates to an absorbent member and a method for forming the same, and more particularly to an absorbent member and a method for forming the same which is suitable for use as an absorbent core in a disposable absorbent article.

BACKGROUND OF THE INVENTION

Absorbent webs which comprise masses of fibers, i.e., fibrous web, are well known in the art. Such webs can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbency characteristics of such fibrous web structures is to incorporate therein superabsorbent material, such as polymeric gelling material (also referred to as hydrogel-forming material superabsorbent polymers, etc.) which imbibe fluid. The superabsorbent material serves to retain fluid such as discharge body liquids. An absorbent structure of this type wherein hydrogel-forming materials in particulate form are incorporated into fibrous webs is disclosed in Weisman and Goldman, U.S. Pat. No. 4,610,678, issued Sep. 9, 1986.

The improvement in absorbency provided by incorporation of absorbent gelling materials has permitted the realization of absorbent articles, such as disposable diapers, which employ relatively thin absorbent cores and which are, therefore, relatively thin products.

Notwithstanding the existence of absorbent cores as described above, there remains a need to provide absorbent cores which reduce and preferably eliminate the phenomena referred to as gel-on-skin. Gel-on-skin is the situation where absorbent gelling materials escape from the absorbent core and travel through the bodyside liner or topsheet of the absorbent article where they come into contact the wearer's skin.

In prior art continuous lay down operations, fibers and superabsorbent materials are mixed together in a continuous web. The continuous web is then cut into individual absorbent members or cores. The individual absorbent members are then placed between a liquid pervious topsheet and a liquid impervious backsheet to form an absorbent article. Unfortunately, this configuration provided an unsatisfactory product as absorbent gelling material easily penetrated through the topsheet creating unacceptable amounts of gel-on-skin.

One solution to the above continuous lay down operation, was to place another web, such as a tissue or nonwoven web on top of the continuous web and then cut both the tissue and continuous web into individual members comprising the core and the tissue. The individual members were then placed in the product with the tissue positioned between the topsheet and the absorbent core substantially preventing absorbent gelling material from escaping from the uppermost surface of the absorbent core and thus reducing the amount of gel-on-skin.

Unfortunately, when for example, the tissue and the continuous web are cut into individual members, the ends of the absorbent core are left open, i.e., the ends of the absorbent core are not covered by the tissue, allowing absorbent gelling material to escape through the ends of the absorbent core.

It is an object of this invention to provide absorbent cores and a method of forming the same via a continuous lay down operation which circumvent the problems of gel-on-skin.

BRIEF SUMMARY OF THE INVENTION

The invention is an absorbent member and a method for forming the absorbent member.

The absorbent member comprises a fibrous material and superabsorbent material. The absorbent member has a perimeter defined by a first side edge, a second side edge, a first end edge and a second end edge. The absorbent member has a pair of discrete, spaced apart, continuous superabsorbent material movement obstruction agent zones. One of the zones is located adjacent the first end edge and the other zone is located adjacent the second end edge.

The absorbent member preferably forms an absorbent core in a disposable absorbent article and is positioned between a liquid pervious topsheet and a liquid impervious backsheet.

To form the absorbent member, a web comprising a fibrous material and superabsorbent material is fed to an applicator. The web has a first side edge and a second side edge. A superabsorbent material movement obstruction agent is applied to the web from the applicator in discrete, spaced apart, continuous zones. The web is then cut through the superabsorbent material movement obstruction agent zones into individual absorbent members having a pair of opposing cut ends.

The individual members have a first surface, a second surface, and a perimeter defined by the first side edge, the second side edge, a first end edge and a second end edge, with the first and second end edges corresponding to the cut ends.

The zones preferably extend from the first side edge to the second side edge, and from the first surface to the second surface.

As used herein the term "superabsorbent material movement obstruction agent" refers an external agent applied to a web comprising fibrous material and superabsorbent material which obstructs the movement of the superabsorbent material through a cut end of the web.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 1 is a plan view of an absorbent article comprising an absorbent core manufactured in accordance with the method of the present invention.

FIG. 2 is a simplified schematic illustration of a continuous lay down method for forming absorbent cores of the present invention.

FIG. 3 is a plan view of a web after the superabsorbent material movement obstruction agent has been applied thereto and prior to being cut into individual absorbent members.

FIG. 4 is a side view of the web of FIG. 3.

FIG. 5 is a plan view of an individual absorbent member.

FIG. 6 is a side view of the individual absorbent member of FIG. 5.

DETAILED DESCRIPTION OF THE INVENTION

The method of the present invention is particularly suitable for manufacturing absorbent cores for use in disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

A preferred embodiment of a unitary absorbent article comprising an absorbent core manufactured by the method of the present invention is the unitary disposable absorbent article, diaper 20, shown in FIG. 1. As used herein, the term "diaper" refers to an absorbent article generally worn by infants and adult incontinent persons and is worn about the lower torso of the wearer. It should be understood, however, that the present invention is also applicable to other absorbent articles such as incontinence briefs, incontinence undergarments, absorbent inserts, diapers holders and liners, feminine hygiene garments, and the like.

With reference to FIG. 1, an absorbent article, such as a diaper 20, generally comprises a liquid pervious topsheet 22, a liquid impervious backsheet 24 joined with the topsheet 22; and an absorbent core 26 intermediate the topsheet 22 and the backsheet 24. The diaper 20 preferably further comprises a front waist region 36, a rear waist region 38, a crotch region 37 positioned between the front waist region 36 and the rear waist region 38, elasticized leg cuffs 28, ear flaps 30, an elastic waist feature 32 and a fastening system 34 comprising at least one tape tab 40. An example of a suitable absorbent article to which the absorbent core of the present invention may be inserted is more fully and completely described in U.S. Pat. No. 5,151,092 issued to Buell et al. on Sep. 29, 1992.

The absorbent core 26 of the present invention may be produced on the apparatus 100, as shown in FIG. 2. In a preferred embodiment, the apparatus 100 is integrated into a disposable absorbent article manufacturing line such that the absorbent core 26 of the present invention may be manufactured "on-line". (As used herein, the term "integrated" means interconnected process modules that operate concurrently to produce finished products from source materials. The term "on-line" is used to refer to the process of manufacturing the absorbent cores of the present invention on an apparatus that is integrated with the manufacturing line that produces the disposable absorbent articles to which the tape tabs will be joined.)

Examining apparatus 100 in greater detail, a web 110 is provided. Web 110 comprises fibrous material and superabsorbent material. The fibrous material may comprise cellulose fibers, in the form of fluff; modified cellulose fibers such as stiffened cellulose fibers; synthetic fibers such as those made of cellulose acetate, polyvinyl fluoride, polyvinylidene chloride, acrylics, polyvinyl acetate, non-soluble polyvinyl alcohol, polyethylene, polypropylene, polyamides (such as nylon), polyesters, bi-component fibers, tri-component fibers, mixtures thereof and the like. Preferred synthetic fibers have a denier of from about 3 denier per filament to about 25 denier per filament, more preferably from about 5 denier per filament to about 15 denier per filament. Also preferably, the fiber surfaces are hydrophilic or are treated to be hydrophilic.

Suitable superabsorbent materials include but are not limited to discrete particles of absorbent gelling material and superabsorbent fibrous material such as acrylate grafted fibers and superabsorbent modified fibers. The superabsorbent material can be in any form which can be incorporated into a flexible web or sheet to form the web 110. The superabsorbent material, upon contact with fluids such as water or body fluids, absorb such fluids. The superabsorbent material is typically in the form of discrete particles of absorbent gelling material.

Continuous web 110 is fed to applicator 120 in the direction indicated by the arrows shown in FIG. 2. Web 110 has a first or uppermost surface 146 and an opposing second or lowermost surface 148. Applicator 120 applies a superabsorbent material movement obstruction agent 122 to the first surface 146 of web 110 in discrete spaced apart zones from one edge of the web 110 to the other edge, i.e., across the entire width of the web. The continuous web 110 is then cut by rotary knife 130 or other cutting device through the superabsorbent material movement obstruction agent zones into individual absorbent members 26.

Of course other webs may be fed with continuous web 110 to applicator 120. For example, a tissue or nonwoven web may be positioned adjacent the first surface 146 and/or the second surface 148 and the composite is then fed to applicator 120. However, for simplicity, only a single web 110 is shown in FIG. 2.

FIG. 3 shows a plan view of the web 110 after the superabsorbent material movement obstruction agent 122 has been applied thereto by applicator 120 and prior to being cut by knife 130. Web 110 has first side edge 140 and an opposing second side edge 142. As can be seen in FIG. 3 the superabsorbent material movement obstruction agent 122 is applied to the web 110 in discrete, spaced apart zones 144 which extend continuously or uninterrupted from the first side edge 140 to the second side edge 142. The zones 144 preferably have a width dimension 170 of from about 0.5 cm to about 20 cm, more preferably of from about 1 cm to about 15 cm, and most preferably from about 2 cm to about 10 cm. The width of the zones 144 needs to be wide enough such that a cut may be made in the web 110 leaving sufficient superabsorbent material movement obstruction agent on either side of the cut.

As shown in FIG. 3 the agent 122 is applied to the web 110 in a rectangular configuration. However, other suitable configurations include but are not limited to, square, oval, dog-bone, elliptical, etc.

FIG. 4 shows a side view of the web 110 of the web of FIG. 3. As can be seen in FIG. 4 the superabsorbent material movement obstruction agent 122 is applied to the web 110 in discrete, spaced apart zones 144 which extend through the entire web 110 from the first surface 146 to the second surface 148. While an agent 122 that did not extend through the entire thickness of the web 110, i.e., from the first surface 146 to the second surface 148, would provide some obstruction to the movement of the superabsorbent material through the cut end of the web 110, it is preferred that the agent extend from the first surface 146 to the second surface 148 to provide the maximum obstruction possible.

FIG. 5 shows a plan view of an individual absorbent member 26 which has been cut from web 110 by knife 130. The absorbent member 26 has a perimeter 158 defined by a first side edge 160, a second side edge 162, a first end edge 163, and a second end edge 165. The first and second end edges 163 and 165 corresponding to the cut ends of the absorbent member 26. The absorbent member 26 has a pair of discrete, spaced apart zones 243 and 245 which extend continuously or uninterrupted from the first side edge 160 to the second side edge 162. Zone 243 is located adjacent first end edge 163 and zone 245 is located adjacent end edge 165. The zones 243 and 245 are the cut portions of zones 144 in continuous web 110. Zones 243 and 245 preferably have a width dimension 270 of from about 0.25 cm to about 10 cm, more preferably of from about 0.5 cm to about 7.5 cm, and most preferably from about 1 cm to about 5 cm.

When viewed from overhead as in FIG. 5, the zones 243 and 245 preferably occupy less than 30% of the absorbent member 26, more preferably less than 20%, and most preferably less than 10%. The percentage is calculated by simply adding the two dimensions 270 together then dividing the summation by the total length dimension 272 of the absorbent member 26 and then multiplying the result by 100. The dimension 275 of the absorbent member 26, typically referred to as the width of the member, does not need to be included in this calculation since the dimension 275 is the same for both the member 26 and the zones 243 and 245.

FIG. 6 shows a side view of the individual absorbent member 26 of FIG. 5. As can be seen in FIG. 6 the superabsorbent material movement obstruction agent 122 is applied to the absorbent member 26 in discrete, spaced apart zones 243 and 245 which extend through the entire absorbent member 26 from the first surface 246 to the second surface 248.

Suitable agents for the superabsorbent material movement obstruction agent include, but are not limited, to polymeric solutions or emulsions, both natural (e.g. natural rubber latex) and synthetic, in which the liquid is water or any other suitable liquid or mixture of liquids. Waterborne emulsions are preferred and more preferred are waterborne emulsions of vinylic and acrylic adhesive polymers.

The superabsorbent material movement obstruction agent is preferably not applied to the entire web, but only in discrete, spaced apart zones. While the superabsorbent material movement obstruction agent does provide the benefit of obstructing the movement of the superabsorbent material through the cut end of a web, it may have some negative effects if applied to the entire web. For example, the agent may increase the stiffness of the web such that it becomes uncomfortable for the wearer if applied to the entire web. The agent may inhibit some of the absorbent properties of the web and thus would negatively impact the absorbent article which employed a web having the agent applied to the entire web. Thus, in order to achieve the desired effect of obstructing the movement of the superabsorbent material through the cut end of a web without negatively impacting the performance, comfort or other properties and characteristics of the web and an absorbent article which employs such a web, the superabsorbent material movement obstruction agent is applied to the web in only discrete, spaced apart zones.

When incorporated into an absorbent article, such as diaper 20 shown in FIG. 1, zones 243 and 244 of absorbent member 26 are preferably positioned within the front waist region 36 and the rear waist region 38, respectively. While, zones 243 and 244 may be of such dimension that they extend into crotch region 37, this is not preferred.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent member comprising:
   a fibrous material and superabsorbents, the absorbent member having a first surface and a second surface, said absorbent member having a perimeter defined by a first side edge, a second side edge, a first end edge, a second end edge;
   a first continuous superabsorbent material movement obstruction agent located adjacent said first end edge;
   a second continuous superabsorbent material movement obstruction agent located adjacent said second end edge, spaced apart from the first continuous superabsorbent material movement obstruction agent;
   the first continuous superabsorbent material movement obstruction agent and the second continuous superabsorbent material movement obstruction agent extend through the absorbent member from the first surface to the second surface, and comprise a material formed from the group of polymeric solutions or emulsions.

2. The absorbent member of claim 1 wherein said superabsorbent material movement obstruction agent zones have a width of from about 0.5 cm to about 5 cm.

3. The absorbent member of claim 1 wherein said superabsorbent material movement obstruction agent zones have a width of from about 1 cm to about 2.5 cm.

4. The absorbent member of claim 1 wherein said absorbent member forms an absorbent core in a disposable absorbent article.

5. The absorbent member of claim 4 wherein said absorbent core is positioned between a liquid pervious topsheet and a liquid impervious backsheet.

6. A method for forming an absorbent member, said method comprising the steps of:
   a) feeding a web comprising a fibrous material and superabsorbent material, said web having a first side edge and a second side edge;
   b) applying a superabsorbent material movement obstruction agent selected from the group of polymeric solutions or emulsions to said web in discrete, spaced apart, continuous zones; and
   cutting said web through said superabsorbent material movement obstruction into individual superabsorbent material movement obstruction agent zones having a pair of opposing cut ends forming a first end edge and a second end edge, wherein said first end edge is at least partially defined by one of said zones and said second end edge is at least partially defined by said other zone; and wherein the continuous superabsorbent material movement obstruction agent extends through the web from the first surface to the second surface.

7. The method of claim 6 wherein said individual members have a first surface, a second surface, and a perimeter defined by said first side edge, said second side edge, a first end edge and a second end edge, said first and second end edges corresponding to said cut ends.

8. The method of claim 6 wherein the zones extend from said first side edge to said second side edge and from said first surface to said second surface.

9. The method of claim 6 wherein said discrete, spaced apart, continuous zones, of superabsorbent material movement obstruction agent have a width of from about 1 cm to about 10 cm.

10. The method of claim 6 wherein said discrete, spaced apart, continuous zones of superabsorbent material movement obstruction agent have a width of from about 2 cm to about 5 cm.

11. The method of claim 7 wherein said polymeric solutions or emulsions are either natural or synthetic.

* * * * *

UNITED STATES PATENT AND TRADEMARK OFFICE
CERTIFICATE OF CORRECTION

PATENT NO. : 6,610,899 B1
DATED : August 26, 2003
INVENTOR(S) : Micahel Divo et al.

Page 1 of 1

It is certified that error appears in the above-identified patent and that said Letters Patent is hereby corrected as shown below:

Column 5,
Line 55, delete "dimension-that" and insert -- dimension that --.

Column 6,
Line 64, delete "claim 7" and insert -- claim 6 --.

Signed and Sealed this

Twenty-first Day of March, 2006

JON W. DUDAS
*Director of the United States Patent and Trademark Office*